United States Patent
Orihara et al.

(10) Patent No.: US 8,355,216 B2
(45) Date of Patent: Jan. 15, 2013

(54) IMAGE PICKUP MODULE AND IMAGE FORMING LENS FOR THE SAME

(75) Inventors: Tatsuya Orihara, Hachioji (JP); Hidetake Segawa, Hachioji (JP); Hironobu Ichimura, Akishima (JP); Mitsujiro Konno, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1280 days.

(21) Appl. No.: 11/939,007

(22) Filed: Nov. 13, 2007

(65) Prior Publication Data

US 2008/0117292 A1 May 22, 2008

(30) Foreign Application Priority Data

Nov. 17, 2006 (JP) .................. 2006-311283

(51) Int. Cl.
*G02B 7/02* (2006.01)
(52) U.S. Cl. ...................... 359/819; 359/811
(58) Field of Classification Search .................. 359/811, 359/819
See application file for complete search history.

(56) References Cited

U.S. PATENT DOCUMENTS

| | | | |
|---|---|---|---|
| 5,424,531 A | 6/1995 | O'Regan et al. | |
| 2002/0131782 A1 | 9/2002 | Yamaguchi et al. | |
| 2004/0215059 A1 | 10/2004 | Homan et al. | |
| 2005/0046010 A1 | 3/2005 | Vittu | |
| 2008/0055748 A1 * | 3/2008 | Konno | 359/819 |

FOREIGN PATENT DOCUMENTS

| | | |
|---|---|---|
| EP | 1 591 818 A1 | 11/2005 |
| JP | 07-159663 A | 6/1995 |
| JP | 11-014804 A | 1/1999 |
| JP | H11-14804 A | 1/1999 |
| JP | 2002-118776 | 4/2002 |
| JP | 2002-350608 | 12/2002 |
| JP | 2003-029157 A | 1/2003 |
| JP | 2005-000320 A | 1/2005 |
| JP | 2005-157290 A | 6/2005 |
| JP | 2005-345919 A | 12/2005 |
| JP | 2006-084621 A | 3/2006 |
| JP | 2006-84621 A | 3/2006 |
| JP | 2003-046825 | 2/2008 |
| WO | WO 2004/070447 A1 | 8/2004 |

* cited by examiner

*Primary Examiner* — Alicia M Harrington
(74) *Attorney, Agent, or Firm* — Arnold International; Bruce Y. Arnold

(57) ABSTRACT

An image forming lens includes a lens element having a flange part that is integral with the lens element. When assembled with an image pickup element to form an image pickup module, an outside perimeter portion of the lens element having a flange part, at a region nearest an image pickup element, is inclined so that outer diameters thereof increase when successively measured at positions nearer to the image pickup element. A frame of the image forming lens according to the invention has an inclined portion on the object side with an outer diameter that becomes smaller when successively measured nearer the object side. Satisfying one or more conditions insures accuracy in assembly and that there will be sufficient room near the object side outside the inclined portion to mount a light source, such as an LED, without having to increase the maximum outer diameter of the image pickup module.

12 Claims, 4 Drawing Sheets

IMAGE PICKUP MODULE AND IMAGE FORMING LENS FOR THE SAME

This application claims benefit of foreign priority under 35 U.S.C. 119 of Japanese Patent Application No. 2006-311283 filed on Nov. 17, 2006, the contents of which are hereby incorporated by reference.

BACKGROUND OF THE INVENTION

1. Field of the Invention

The present invention relates to an image pickup module that includes a lens element having a flange part that is integral with the lens element and, in particular, relates to a small and thin image pickup module that is suitable for use in an endoscope. Also, the present invention relates to an image forming lens that includes a lens element having a flange part that is integral with the lens element, for use with an image pickup module.

2. Description of the Related Art

In conventional image pickup modules it has been proposed that, in order to reduce costs and manufacturing errors, some lens elements of the image pickup module be formed integrally with a flange part so that the number of components may be reduced, thereby improving the ease of assembly of the image pickup module. One such image pickup module, for example, is disclosed in Japanese Laid-open Patent Application No. 2003-46825. On the other hand, in an image pickup module suitable for use in an endoscope, etc., it has been required that the diameter of the image pickup module be as small as possible in order to minimize the burden to a patient and to improve an operator's performance. Therefore, in an image pickup module that includes a lens element having a flange part that is integral with the lens element, it is particularly important to miniaturize the outer diameter of the image pickup module as much as possible. However, with respect to the conventional image pickup module equipped with a lens element integrally formed with a flange part as disclosed in Japanese Laid-open Patent Application No. 2003-46825, nothing has been proposed for miniaturizing the outer diameter of that lens element.

In general, in an image pickup module that includes a lens element having a flange part that is integral with the lens element, at the time of assembly of the image pickup module, positional adjustment of the lens element in the axial direction is usually achieved by abutting one end of the lens element that is formed integrally with a flange part to the image pickup surface of the image pickup element. Accordingly, in order to obtain a high accuracy in positioning the lens element in the axial direction, a high accuracy in manufacturing the lens element that is formed integrally with the flange part is required.

BRIEF SUMMARY OF THE INVENTION

The image pickup module according to the present invention includes a lens element having a flange part that is integral with the lens element, and an image pickup element that is arranged in the light path following the lens element having a flange part. An outside perimeter surface of the lens element having the flange part, at a portion nearest the image pickup element side, is inclined so that the outer diameter of the flange part increases when measured successively at a position nearer to the image pickup element side.

In the image pickup module according to the present invention, it is desired that the image forming lens has a frame for holding the outside perimeter portion of one or more lens elements, with an outside perimeter surface of the frame on the object side being inclined so that its diameter increases when successively measured nearer to the image pickup element side.

Also, in the image pickup module according to the present invention, it is desired that an inner circumferential surface of the frame on the image side be inclined so that the frame has a larger inner diameter when successively measured nearer the image pickup element side. Moreover, it is desired that the amount of inclination of this inclined circumferential surface be such that, during assembly of the image pickup module, a small clearance forms between it and the outside perimeter surface of the flange part, which clearance becomes larger towards the image pickup element side.

Further, it is preferred that the lens having a flange part be manufactured by injection molding so that a mark of a gate may be located near the image pickup element.

In the image pickup module according to the present invention, it is preferred that the image forming lens be formed of two or more lens elements, with the outer diameter of each of the lens elements becoming smaller the nearer the particular lens element is to the object side.

The above discussed features, as well as other features and advantages of the present invention, will become apparent from the following detailed description of the preferred embodiments when considered in conjunction with the accompanying drawings.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

Figure 1:
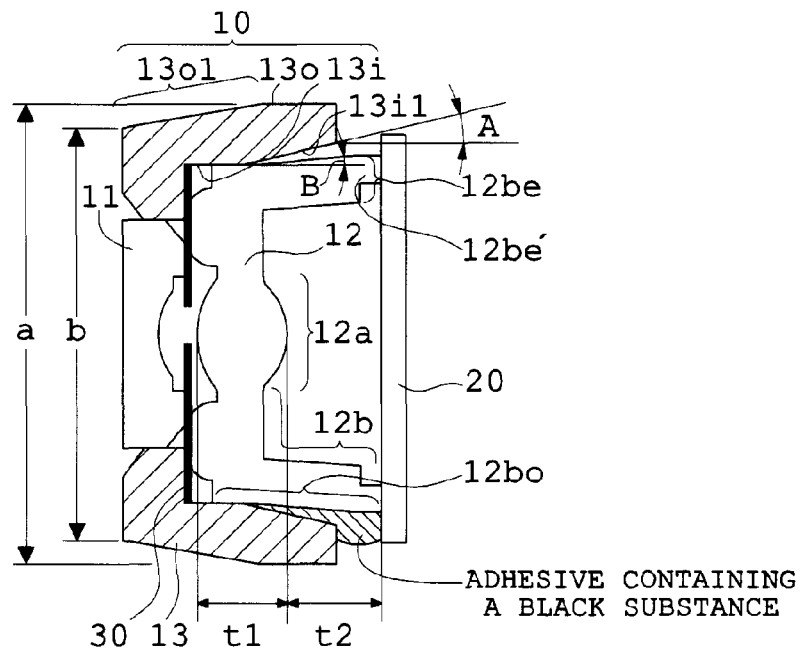
FIG. 1 shows an image pickup module according to Embodiment 1 of the present invention.

As will be discussed in detail below, in a first embodiment of the image pickup module according to the present invention, it is desired that the frame is formed of a light-blocking material that is arranged so as to cover all, or nearly all, of the outside perimeter surface of the lens elements of the image forming lens. In a second embodiment of the image pickup module according to the present invention, it is desired that the frame is formed of a light-blocking material that is arranged so as to cover a portion of the outside perimeter surfaces of the lens elements of the image forming lens. Moreover, in the second embodiment, a light-blocking component is arranged in the outside perimeter surface(s) of the lens element or lens elements not entirely covered by the frame. It is desired that the light-blocking component be an adhesive that contains a black substance, such as black paint or black pigment.

The image forming lens for the image pickup module according to the present invention is characterized by including a lens element having a flange part, and is used in an image pickup module with the lens element having the flange part arranged abutting the image pickup element. An outside perimeter surface of the lens element having a flange part, at a region nearest the image pickup element, is inclined so that outer diameters of the flanged lens element increase in said region when successively measured at positions nearer the image pickup element.

In the image pickup module according to the present invention, it is desired that the lens element having the flange part is manufactured by injection molding, with a mark of a gate used in the injection molding process being located near the image pickup element.

It also is desired that the image forming lens includes two or more lens elements, arranged in order from the object side, with an outer diameter of the lens element positioned nearest the object side being less than any outer diameters of the lens element having a flange part.

Moreover, it is desired that the image forming lens has a frame for holding the lens element or lens elements, and that an outside perimeter surface of the frame has an inclined portion on the object side of the frame that is inclined so that its diameter increases when successively measured at positions nearer the image pickup element side.

In addition, it is desired that an inner circumferential surface of the frame has an inclined part on the image pickup module side that is inclined so that its diameter increases when successively measured nearer the image pickup element side. Moreover, the inclination amount is different than the inclination amount of the outside perimeter surface of the flanged lens element at a region nearest the image pickup element so that a small clearance, between the inner circumference surface of the frame and the outside perimeter surface of the flange part, increases when successively measured at positions nearer the image pickup element side, and this clearance is formed when the image pickup module is assembled.

In the image forming lens for the image pickup module according to the present invention, it is desired that the frame is formed of a light-blocking material and is arranged so as to cover all, nearly all, or part of the outside perimeter surface of the lens element or lens elements that form the image forming lens. A light-blocking component may be arranged on the outside perimeter surface of one or more of the lens elements that comprise the image forming lens so as to prevent stray light that is not blocked by the frame fully covering the outside perimeter surfaces of the lens element(s) from reaching the image pickup element. The light-blocking component may be, for example, an adhesive that contains a black substance.

The image pickup module according to the present invention can readily be designed by those of ordinary skill for use in either an endoscope or a microscope.

In the image pickup module according to the present invention, it is preferred that the following Condition (1) is satisfied:

$$t2/t1 > 0.8 \qquad \text{Condition (1)}$$

where
  $t1$ is the thickness of the center of the optical part of the lens element that is nearest the image pickup element, and
  $t2$ is the distance from the image-side surface of the center part of the optical part of the lens element nearest the image pickup element to the image pickup element.

Figure 3A:
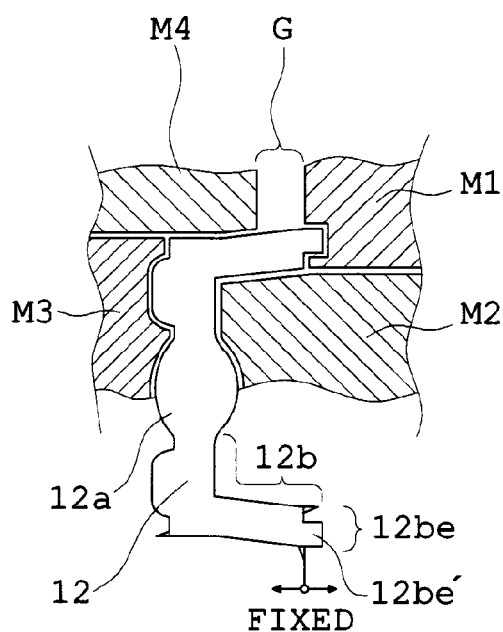
FIG. 3A is a sectional view, of a section that includes the optical axis of a lens element having a flange part that is integral with the lens element, and also shows the molding components used in making the lens element having a flange part that may be used in the image pickup modules shown in FIGS. 1 and 2.

Since a gate G that is used for injection molding of the lens element 12 is arranged in the flange part 12b at a position near the image pickup element 20 so that a mark of the gate is near the image pickup element 20, the structure of various molding dies used for the injection molding of the lens element 12 may be as shown in FIG. 3A.

As shown in FIG. 3A, the lens element 12 is surrounded by: a molding die M1 that forms an end part 12be of the flange part 12b and a touching part 12be' that touches the image pickup element 20; a molding die M2 that forms the inner side of the flange part 12b and the lens element part 12a; a molding die M3 that forms the object side of the flange part 12b and the lens element part 12a; and a molding die M4 that forms the outside of the flange part 12b. Accordingly, the part that forms the touching part 12be' is made short in the axial direction by satisfying Condition (1) above, thereby enabling a channel of the melted resin from the gate G to be minimized in length. Therefore, it becomes easy to carry out processing in the axial direction of the touching part 12be' of the flange part 12b, and accordingly, it becomes possible to make assembly of the image pickup module, more specifically, assembly of the touching part 12be' to the image pickup element 20 highly accurate.

Figure 3B:
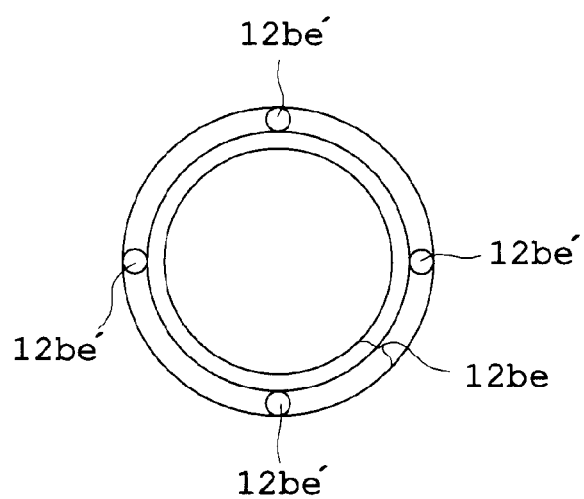
FIG. 3B is a view of the lens element having a flange part that is integral with the lens element as viewed in the axial direction from the side that faces the image pickup element (in the case where the lens element is mounted so as to abut the image pickup element)

FIG. 3B is a view of the lens element having a flange part that is integral with the lens element as viewed in the axial direction from the side that faces the image pickup element (in the case where the lens element is mounted so as to abut the image pickup element). As can be seen, there are multiple touching parts 12be' spaced near the outer perimeter of the end part 12be.

When the above Condition (1) is satisfied, the flange part 12b becomes long in the axial direction, and accordingly, an effect of miniaturizing the outer diameter of the entire image pickup module (due to the tapering formed in the outside perimeter portion 12bo) can be more easily obtained.

Moreover, in the image pickup module according to the present invention, it is also desired that the following Condition (2) is satisfied:

$$A/B > 1.5 \qquad \text{Condition (2)}$$

where
  A is the taper angle of the inner circumference portion of the frame, and
  B is the taper angle of the outside perimeter portion of a lens element of the image forming lens of the image pickup module.

Figure 2:
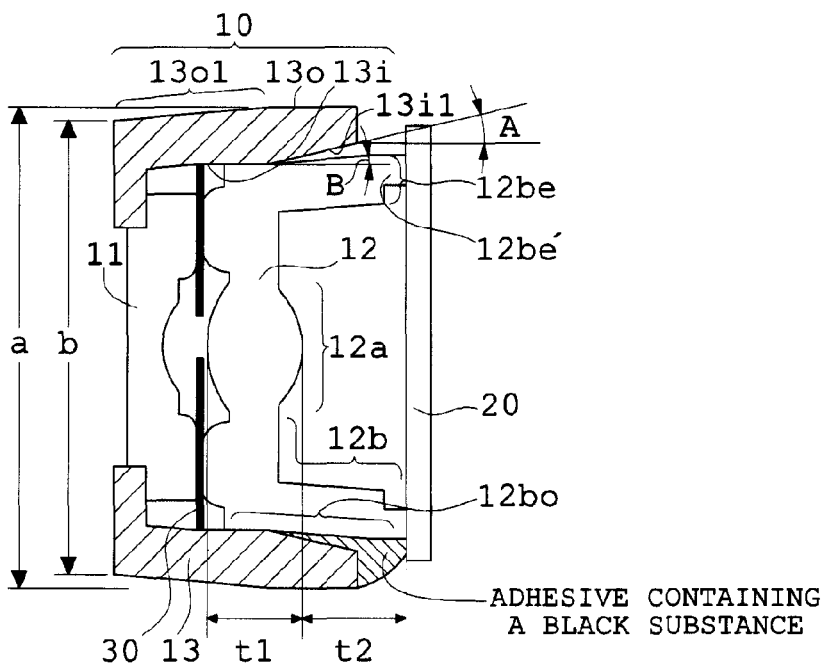
FIG. 2 shows an image pickup module according to Embodiment 2 of the present invention.

Referring to FIG. 1, the image pickup module of the present invention includes an image forming lens 10 and an image pickup element 20. In FIGS. 1 and 2, item 30 is an aperture stop. The image forming lens 10 includes two or more lens elements 11 and 12, in order from the object side, as well as a frame 13. The lens element 12 is manufactured by injection molding, and includes a flange part 12b that is integrally formed with a lens part 12a. In FIG. 3A, G is a gate position used at the time of the injection molding. A gate G is arranged in the flange part 12b at a position which is near the image pickup element 20, and a mark of the gate (the mark is not shown) remains in a corresponding part of the flange part 12b. The lens element 12 is injection molded so that the outside-perimeter-part 12bo of the flange part 12b has an inclination such that the diameter thereof becomes larger as successive measurements are taken nearer to the image pickup element 20 side. The lens element 11 is formed with an outer diameter smaller than any outer diameter of the lens element 12. The frame 13 is manufactured of a light-blocking material. Moreover, the frame 13 holds all or a predetermined part of the outside perimeter portion of each lens element that is included in the image forming lens, and is arranged so as to cover at least a part of the outside perimeter portion of the lens elements 11 and 12. In the event the frame does not cover all of the outside perimeter portion of a lens element or flange part, any outside perimeter portion of the lens elements 11 and 12 not covered by the frame 13 will have a light-blocking material applied thereto, such as a light-blocking adhesive.

The outside perimeter surface 13o of the frame 13 includes inclined part 13o1 that is inclined so that the diameter thereof becomes larger when successively measured at positions nearer the image pickup element 20. The inner circumference portion 13i of the frame 13 has an inclined part 13i1 that is inclined so that its diameter also becomes larger when successively measured at positions nearer the image pickup element 20.

According to the image pickup module of the present invention, an inner circumference portion of the frame has an inclined part on the image pickup element side that is inclined so that its diameter increases when successively measured nearer the image pickup element side, with the inclination amount being different than the inclination amount of the outside perimeter portion of the lens element having a flange part at a region nearest the image pickup element. The difference in inclinations is such that a small clearance that forms, between the inner circumference portion of the frame and the outside perimeter portion of the flange part, when the image pickup module is assembled, increases when successively measured at positions nearer to the image pickup element side.

According to the image pickup module of the present invention, since the outside perimeter surface 13o of the frame 13 is formed to have the inclined part 13o1 inclined so that its diameter becomes smaller when successively measured nearer the object side, the outer diameter b at the object side becomes smaller than the outer diameter a of the frame 13. Therefore, the outer diameter of the image pickup module having the lens element 12 with the flange part 12b can be miniaturized on the object side of the image pickup module, thereby allowing space for arranging a light source, such as an LED, that is secured to the object side of the image pickup module. In this way, a smaller-diameter module than in the prior art (not only of the tip end, but of the entire module) may be provided.

Furthermore, the outside-perimeter-part of the lens element 12 is arranged to have an inclination so that its diameter becomes smaller when successively measured nearer the object side, (i.e., it becomes larger when successively measured nearer to the side of the image pickup element 20), and the inner circumference portion 13i of the frame 13, is formed with an inclined part 13i1 that is inclined so that its diameter becomes smaller when successively measured nearer the object side, (i.e., the inner circumference increases when successively measured nearer to the image pickup element 20). Moreover, the two inclinations are different so that, when assembled, a small clearance between the outside perimeter portion 12bo of the flange part 12b and the frame becomes larger nearer the image pickup element 20. Therefore, the outer diameter of the entirety of the image pickup module having the lens element 12 with the flange part 12b can be miniaturized, thereby allowing a space for a light source, such as an LED, to be secured to the object side of the image pickup module without enlarging the module as a whole, as required in the prior art. Satisfying Condition (2) above assists in insuring that a sufficient space for a light source, such as the LED, is provided.

The miniaturization effect of the image pickup module according to the present invention becomes remarkable when it is used for optical devices for which miniaturization is greatly demanded, such as a capsule endoscope or even a common endoscope. Several Embodiments of the invention will now be discussed in detail.

Embodiment 1

Figure 4A:
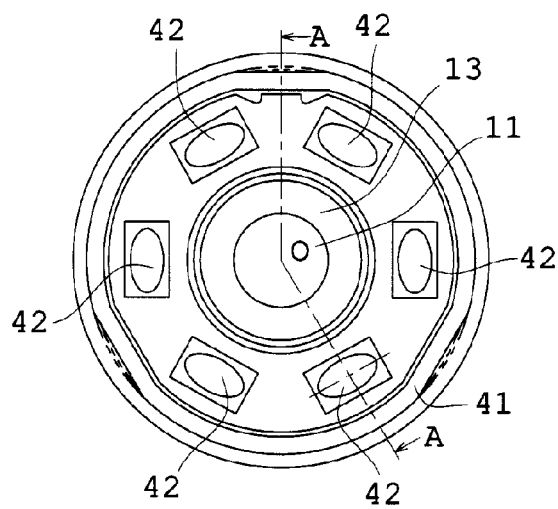
FIGS. 4A and 4B show axial and sectional views, respectively, of a capsule endoscope that includes the image pickup module according to Embodiment 1 of the present invention, with FIG. 4A being an axial view of the capsule endoscope as seen from the object side, and with FIG. 4B being a sectional view along the lines A-A shown in FIG. 4A.
Figure 4B:
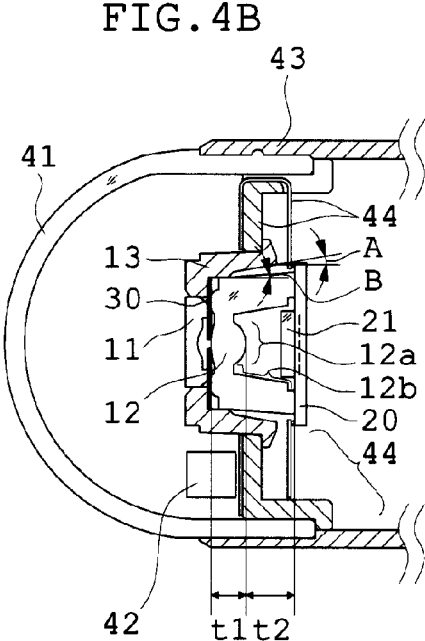

FIGS. 4A and 4B show axial and sectional views, respectively, of a capsule endoscope that includes the image pickup module according to Embodiment 1 of the present invention, with FIG. 4A being an axial view of the capsule endoscope as seen from the object side, and with FIG. 4B being a sectional view along the lines A-A shown in FIG. 4A.

The capsule endoscope of FIGS. 4A and 4B includes a transparent cover 41 and two or more lighting components 42 (that, for example, may be formed of LEDs), and an image pickup module.

The transparent cover 41 is arranged at the tip of the housing for the main part of the endoscope 43. In the image pickup module of Embodiment 1, the fundamental composition of the image pickup module is the same as shown in FIG. 1. In FIG. 4B, item 21 is a cover glass that covers the image pickup surface of the image pickup element. A substrate part 44 is arranged inside the tip of the housing for the main part of the endoscope 43.

The image pickup module is attached to the central part of the substrate part 44, and further, the lighting components 42 are arranged annularly and attached between the image pickup module and the housing for the main part of the endoscope 43 in the substrate part 44.

In the capsule endoscope of FIGS. 4A and 4B, as for the lens element 12, the thickness t1 is 1 mm, the distance t2 is 1.3 mm, and the ratio t2/t1 equals 1.3. Thus, Condition (1) is satisfied by this embodiment. Furthermore, the taper angle A is 10 degrees, the taper angle B is 5 degrees, and thus the ratio A/B equals 2. Therefore, Condition (2) is satisfied by this embodiment.

Embodiment 2

Figure 5A:
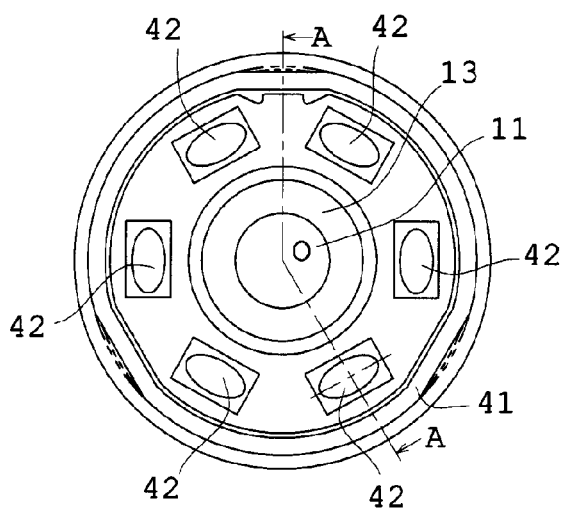
FIGS. 5A and 5B show axial and sectional views, respectively, of a capsule endoscope that includes the image pickup module according to Embodiment 2 of the present invention, with FIG. 5A being an axial view of the capsule endoscope as seen from the object side, and with FIG. 5B being a sectional view along the lines A-A shown in FIG. 5A.
Figure 5B:
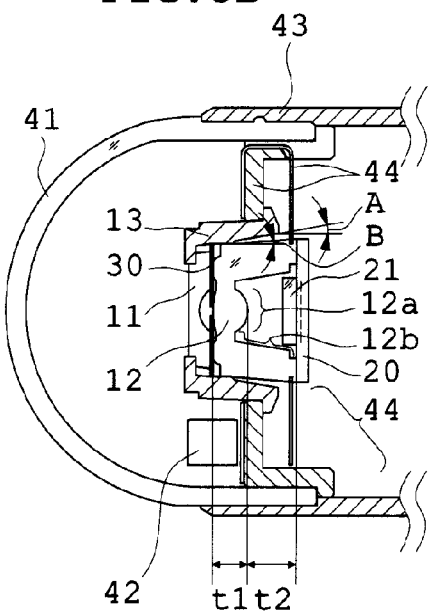

FIGS. 5A and 5B show axial and sectional views, respectively, of a capsule endoscope that includes the image pickup module according to Embodiment 2 of the present invention, with FIG. 5A being an axial view of the capsule endoscope as seen from the object side, and with FIG. 5B being a sectional view along the lines A-A shown in FIG. 5A. In the capsule endoscope of FIGS. 5A and 5B, the fundamental constitution of the image pickup module is the same as for Embodiment 2 shown in FIG. 2. This Embodiment is similar to that of Embodiment 1, so that both Condition (1) and Condition (2) above are satisfied by this embodiment.

Embodiment 3

Figure 6:
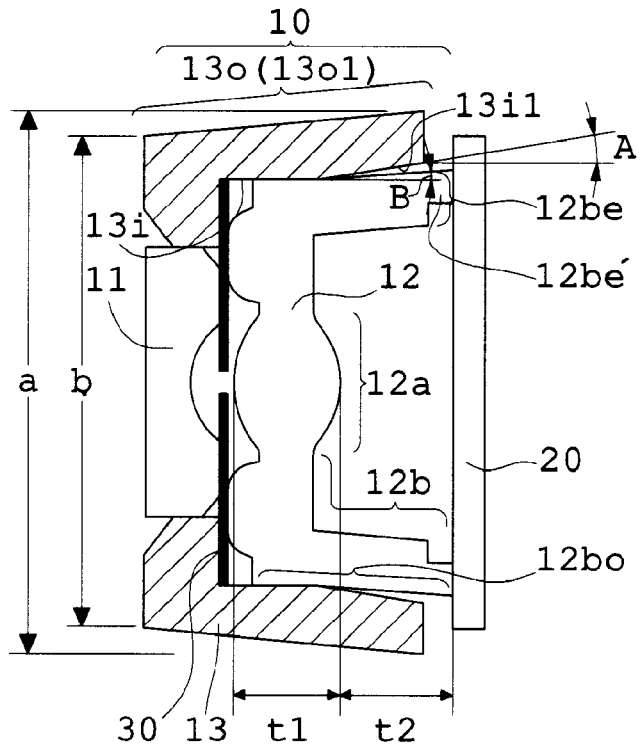
FIG. 6 is a sectional view showing an image pickup module according to Embodiment 3 of the present invention for use in a capsule endoscope.

FIG. 6 is a sectional view showing an image pickup module according to Embodiment 3 of the present invention for use in a capsule endoscope. In the capsule endoscope of Embodiment 3, the fundamental composition of the image pickup module is the same as the image pickup module of Embodiment 1 shown in FIG. 1. In this embodiment, for the lens element 12, the thickness t1 is 1.15 mm, the distance t2 is 1.15 mm, and thus the ratio t2/t1 equals 1.0. Furthermore, the taper angle A is 6 degrees, the taper angle B is 4 degrees, and thus the ratio A/B equals 1.5. Therefore, both Condition (1) and Condition (2) above are satisfied by this embodiment.

Embodiment 4

Figure 7:
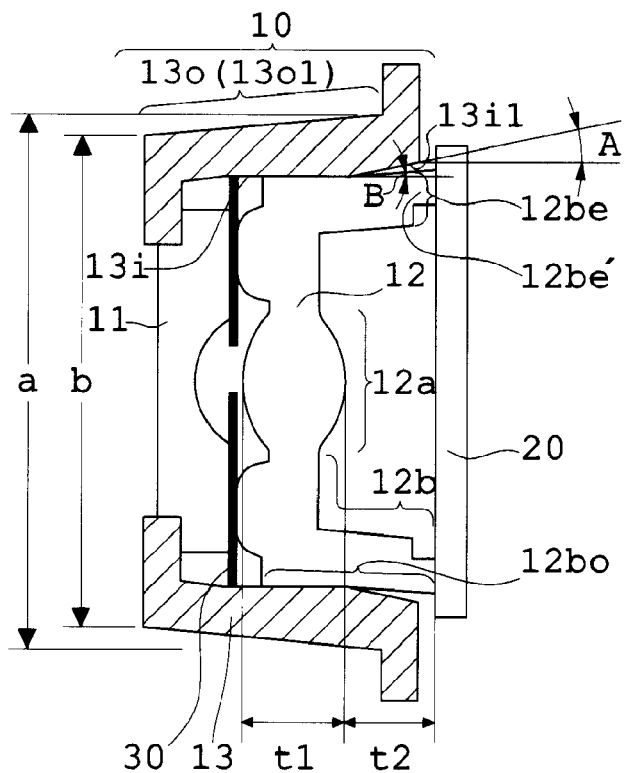
FIG. 7 is a sectional view showing an image pickup module according to Embodiment 4 of the present invention for use in a capsule endoscope.

FIG. 7 is a sectional view showing an image pickup module according to Embodiment 4 of the present invention for use in a capsule endoscope. In the capsule endoscope of Embodiment 4, the fundamental composition of the image pickup module is the same as for Embodiment 2 shown in FIG. 2.

In the capsule endoscope according to this embodiment, for the lens element 12 that is arranged nearest the image pickup element 20, the thickness t1 is 0.8 mm, the distance t2 is 0.65 mm, and thus the value of t2/t1 equals 0.8125. Furthermore, the taper angle A is 9 degrees, the taper angle B is 3 degrees, and thus the ratio A/B equals 3.0. Therefore, both Condition (1) and Condition (2) above are satisfied by this embodiment.

In the case of a small observation device such as an endoscope, the lighting component(s) thereof are generally arranged around the image pickup module. On the other hand, since lighting components often have been standardized, arbitrary miniaturization of these components is difficult.

In an observation device such as a capsule endoscope, the decrease in burden to a patient by miniaturization can be very significant even though the actual amount of miniaturization is rather small. According to the capsule endoscopes of Embodiments 1-4 shown in FIGS. 4A-7, since the image pickup module of the present invention is used, the diameter of the entire image pickup module can be miniaturized. This enables the entire capsule endoscope diameter to be miniaturized, while still providing sufficient space for lighting components to be arranged near the periphery of the image pickup module. Furthermore, the touching part 12be' of the flange part 12b of the lens element 12 can be formed with a high degree of accuracy, and the positioning of the lens element 12 relative to the image pickup element 20 can be achieved with a high degree of accuracy at the time of manufacturing the image pickup module.

Explanations concerning the image pickup module have been provided in the embodiments mentioned above. However, even in the case wherein the image forming lens 10 is constituted as a single unit that is then combined with an arbitrary image pickup element, the same performance and effects as for the image pickup modules discussed above can be obtained.

The invention being thus described, it will be obvious that the same may be varied in many ways. For example, the image forming lens 10 is not limited to being formed of only two lens elements, such as by using lens elements 11 and 12 discussed above, as it may also be formed using three or more lens elements. In such a case, the lens element nearest to the image pickup element should be formed integral with a flange part, just as the lens element 12 is formed in the embodiments mentioned above. The image pickup module according to the present invention is useful in any field wherein an observation device is required that is equipped with a small image pickup element, and for which miniaturization and high accuracy positioning are necessary. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An image pickup module comprising:
   an image forming lens that includes a flanged lens element, the flanged lens element having an optical part and a flange part that are integral with each other; and
   an image pickup element that is arranged adjacently behind the flanged lens element, to receive light from the image forming lens; wherein
   the image forming lens further includes a frame for holding the flanged lens element or lens elements including the flanged lens element, of the image forming lens,
   an outside perimeter surface of the flanged lens element, at an end region nearest the image pickup element, is inclined so that, in the end region, the flanged lens element has a larger outer diameter as measured at a position nearer the image pickup element, and
   an outside perimeter surface of the frame has an inclined portion on an object side of the frame that is inclined so that the frame has a larger outer diameter as measured at a position nearer the image pickup element.

2. The image pickup module according to claim 1, wherein an inner circumferential surface of the frame has an inclined portion on an image pickup element side that is inclined so that the frame has a larger inner diameter as measured at a position nearer the image pickup element, an inclination amount of the inner circumferential surface of the frame being different than an inclination amount of the outside perimeter surface of the flanged lens element at the end region nearest the image pickup element so that a clearance is formed between the inner circumferential surface of the frame and the outside perimeter surface of the flange part, and the clearance comes to be greater as measured at a position nearer the image pickup element.

3. The image pickup module according to claim 2, wherein the following condition is satisfied:

$$A/B > 1.5$$

where
   A is a taper angle of the inner circumferential surface of the frame, and
   B is a taper angle of the outside perimeter surface of the flanged lens element of the image forming lens.

4. The image pickup module according to claim 1, wherein the frame is formed of a light-blocking material and is arranged to cover nearly all of an outside perimeter portion of the flanged lens element or lens elements including the flanged lens element that form the image forming lens.

5. The image pickup module according to claim 1, wherein the frame is formed of a light-blocking material and is arranged to cover a part of an outside perimeter portion of the flanged lens element or lens elements including the flanged lens element that form the image forming lens; and a light blocking component is arranged at a remaining part of the outside perimeter portion of the flanged lens element or lens elements including the flanged lens element, of the image forming lens, which fails to be covered by the frame.

6. The image pickup module according to claim 5, wherein the light blocking component is an adhesive which contains black paint.

7. An image forming lens for use in an image pickup module in combination with an image pickup element, the image forming lens defining an object side and an image side so that the image pickup element is arranged on the image side of the image forming lens, the image forming lens comprising:

a flanged lens element having an optical part and a flange part, the flange part having a plurality of precisely formed abutting portions to abut on the image pickup element, to thereby accurately position the flanged lens element in an axial direction relative to the image pickup element; wherein the image forming lens further includes a frame for holding the flanged lens element or lens elements including the flanged lens element, of the image forming lens, an outside perimeter surface of the flanged lens element is, at an image-side end region, inclined so that the flanged lens element has a larger outer diameter as measured at a position nearer the image side, and an outside perimeter surface of the frame has an inclined portion on the object side of the frame that is inclined so that the frame has a larger outer diameter as measured at a position nearer the image side.

8. The image forming lens according to claim 7, wherein an inner circumferential surface of the frame has an inclined portion on the image side that is inclined so that the frame has a larger inner diameter as measured at a position nearer the image side, an inclination amount of the inner circumferential surface of the frame being different than an inclination amount of the outside perimeter surface of the flanged lens element at the image-side end region so that, when the image pickup module is assembled, a clearance is formed between the inner circumferential surface of the frame and the outside perimeter surface of the flange part and the clearance comes to be greater as measured at a position nearer the image side.

9. The image forming lens according to claim 8, wherein the following condition is satisfied:

A/B>1.5 where
  A is a taper angle of the inner circumferential surface of the frame, and
  B is a taper angle of the outside perimeter surface of the flanged lens element.

10. The image forming lens according to claim 7, wherein the frame is formed of a light-blocking material and is arranged to cover nearly all of an outside perimeter portion of the flanged lens element or lens elements including the flanged lens element that form the image forming lens.

11. The image forming lens according to claim 7, wherein the frame is formed of a light-blocking material and is arranged to cover a part of an outside perimeter portion of the flanged lens element or lens elements including the flanged lens element that form the image forming lens, and a light blocking component is arranged at a remaining part of the outside perimeter portion of the flanged lens element or lens elements including the flanged lens element, of the image forming lens, which fails to be covered by the frame.

12. The image forming lens according to claim 11, wherein the light blocking component is an adhesive which contains black paint.

* * * * *